United States Patent
Jacome et al.

(10) Patent No.: US 10,668,262 B2
(45) Date of Patent: Jun. 2, 2020

(54) PELLET IMPLANTATION DEVICE AND TOOL KIT

(71) Applicants: Pellecome LLC, Randolph, NJ (US); Enrique Jacome, Indian Wells, CA (US); Richard Costa, Bedminster, NJ (US); Sean Ely, Flemington, NJ (US); Mitchell Tung, Basking Ridge, NJ (US)

(72) Inventors: Enrique Jacome, Indian Wells, CA (US); Richard Costa, Bedminster, NJ (US); Sean Ely, Flemington, NJ (US); Mitchell Tung, Basking Ridge, NJ (US)

(73) Assignee: Pellecome LLC, Randolph, NJ (US)

( * ) Notice: Subject to any disclaimer, the term of this patent is extended or adjusted under 35 U.S.C. 154(b) by 0 days.

(21) Appl. No.: 15/746,016

(22) PCT Filed: Dec. 21, 2017

(86) PCT No.: PCT/US2017/067849
§ 371 (c)(1),
(2) Date: Jan. 19, 2018

(87) PCT Pub. No.: WO2019/125457
PCT Pub. Date: Jun. 27, 2019

(65) Prior Publication Data
US 2019/0290894 A1    Sep. 26, 2019

(51) Int. Cl.
*A61M 37/00* (2006.01)
*A61B 17/34* (2006.01)
*A61B 17/3211* (2006.01)
*A61D 7/00* (2006.01)

(52) U.S. Cl.
CPC ..... *A61M 37/0069* (2013.01); *A61B 17/3211* (2013.01); *A61B 17/3468* (2013.01); *A61D 7/00* (2013.01); *A61M 37/00* (2013.01); *A61B 2017/32113* (2013.01); *A61M 2210/04* (2013.01); *A61M 2250/00* (2013.01)

(58) Field of Classification Search
CPC .......... A61B 5/150175; A61B 5/15019; A61B 5/150198; A61B 17/3468; A61B 2017/32113; A61M 37/0069; A61M 31/007; B26B 29/02; B26B 5/003
See application file for complete search history.

(56) References Cited

U.S. PATENT DOCUMENTS

| | | | | |
|---|---|---|---|---|
| 3,906,626 A * | 9/1975 | Riuli | ................... | A61B 17/3213 30/162 |
| 4,451,254 A * | 5/1984 | Dinius | .............. | A61M 37/0069 206/535 |
| 6,190,350 B1 * | 2/2001 | Davis | ................ | A61M 37/0069 604/61 |
| 2004/0199140 A1 * | 10/2004 | Rue | ..................... | A61B 17/3468 604/506 |
| 2006/0241664 A1 * | 10/2006 | Lam | ................... | A61B 17/3211 606/167 |

(Continued)

*Primary Examiner* — Emily L Schmidt
(74) *Attorney, Agent, or Firm* — Mitchell J Mehlman, Esq.

(57) ABSTRACT

Medicinal pellet insertion devices and kits including sterile loading sheaths and scalpels for making predetermined incisions are provided. The devices and kits can be used in the treatment of patients with controlled, sustained release medicinal pellets implanted by subcutaneous insertion.

15 Claims, 16 Drawing Sheets

(56) References Cited

U.S. PATENT DOCUMENTS

| | | | |
|---|---|---|---|
| 2007/0021714 A1* | 1/2007 | Miller | A61M 37/0069 604/60 |
| 2009/0157110 A1* | 6/2009 | Muto | A61B 17/3211 606/167 |
| 2018/0256108 A1* | 9/2018 | Au-Yeung | A61B 5/686 |

* cited by examiner

FIG. 23
FIG. 24
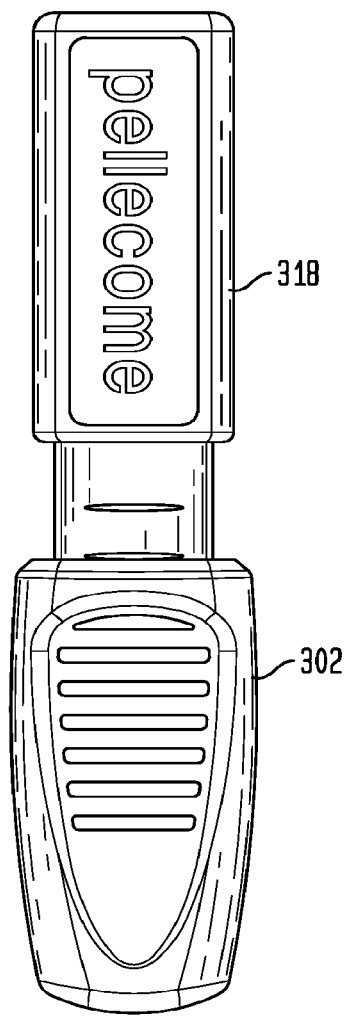
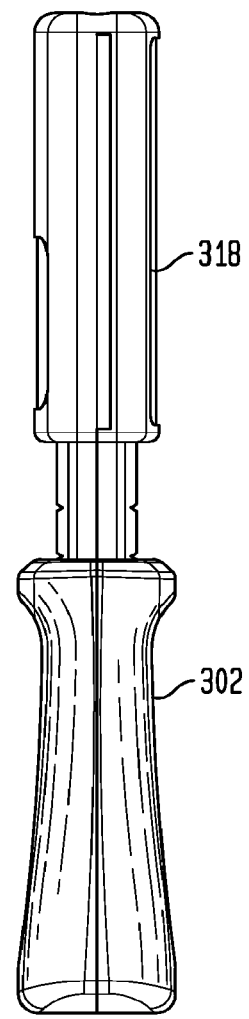

PELLET IMPLANTATION DEVICE AND TOOL KIT

BACKGROUND OF THE INVENTION

The instant invention relates to a pellet implantation devices and tools including kits for implanting therapeutic pellets subcutaneously into a patient. The invention relates more specifically to mechanical devices designed for subcutaneous implantation of potentially fragile medicinal pellets, such as hormone pellets that act at a constant rate over a prolonged period of time used largely in treating mammalian subjects.

An implantation procedure is typically related to subcutaneously implanted hormone pellets but could be used in similar applications for other medicaments. The individual pellets are typically smaller than a grain of rice and are implanted into the subcutaneous tissue, where they provide a slow continuous release of hormone or other medicaments into the bloodstream. It is imperative that the implantation device does not damage the pellets as any such damage that changes the release rate could have serious consequences for a patient.

The pellets can be implanted in the lower abdomen or buttocks in a physician's office with the use of a local anesthetic and a small controlled incision for insertion. The release of the drug can continue over a 3-6-month period or longer.

The kit can include a pellet loading tool designed to easily load a hollow needle with pellets while maintaining sterility of both the pellets and the needle and protecting the user, a medical professional, from injury.

A sheathed scalpel included in the kit is used to make a tailored incision at a preselected area for insertion. After the needle is inserted through the incision and into the patient, the operator presses a tab causing the needle to retract thus carefully deploying the pellets in a linear single file without disturbing the alignment of the pellets nor their structural integrity. Once the device is removed, the incision can be closed with surgical glue or other known closure methods.

U.S. Pat. No. 3,402,712 discloses a gravity-feed pellet implanter has a tooth-engaging notch on the side of its plunger rod near its distal end, and a toothed cam extending into the plunger-containing bore and spring-biased against the notched side of the plunger; the toothed cam prevents advance of the plunger unless a pellet is in transport and prevents movement of pellets toward the needle unless the plunger is being advanced.

U.S. Pat. No. 4,154,239 discloses an implanter by which pelleted drugs can be inserted or implanted under the skin of an animal typically to promote fattening of beef cattle and the like. The device includes a thrust pin which can be pushed through a tube containing the pellets to eject them into and through a hollow needle at the front of the device. A mechanism acts on the pin to push it in the forward direction and a return spring acts to return it to its rest position.

U.S. Pat. No. 5,147,295 discloses an implanting gun apparatus. A drive rod is linearly moveable in a handle assembly by a first pivotable linkage actuated by a trigger, to urge a pellet from a carrier through a head assembly and into a needle. A second pivotable linkage, also actuated by the trigger, retracts the needle, the head assembly, and the carrier into the handle after the pellet has been urged into the needle. The gun apparatus is particularly adapted to implant pellets in animals, particularly as medicament pellets.

U.S. Pat. No. 7,850,639 discloses a device for inserting implantable objects beneath the skin of a patient includes a handle for grasping the device and a base connected to the handle. The base comprises a post, a cannula, and a flexible actuator positioned in an angled track. The cannula is positioned coaxially around and is longitudinally slidable over the post from an extended position, where an implantable object is retained in the cannula, to a retracted position, where the implantable object is released from the cannula. A flexible actuator positioned on an angled track in the base is slidably engaged with a boss on the cannula and is used to move the cannula from an extended position to a retracted position to release the implantable object from the cannula; the actuator flexes between a locked and an unlocked position. The angled track provides for control of the release of the implantable object.

The present invention provides numerous advantages over known devices. The instant invention includes devices, tools, and kits for improving the ease, consistency, sterility, and delivery of subcutaneous medicaments, such as hormone pellets, while reducing the risk of complications from contamination, the risk of injury to the operator, and the frequency of treatments required.

SUMMARY OF THE INVENTION

In one aspect of the invention a pellet implantation device includes a housing. The housing can have a first aperture and a second aperture. A slider tab can be recessed in the first aperture and slidably connected to the housing. A capture bracket can be connected to the slider tab. The capture bracket can include a first flange. A ram can be mounted within the housing. The ram can include a second flange for mounting a spring. A needle can include a distal flange and a proximal end. The distal flange can be mounted within the second aperture of the housing. The needle can be configured to store pellets therein.

In one embodiment of this aspect, the capture bracket can include a locking tab and the housing can include a recess for capturing the locking tab, thereby locking the device so that the needle can only be retracted once after a delivery of pellets to a patient.

In some embodiments of this aspect, the needle can include a spring clip mounted within an aperture. The spring clip can retain the pellets within the needle prior to the pellets being dispensed subcutaneously.

In certain embodiments, the device can include a needle sheath.

In some embodiments of this aspect, the device can further include a needle sheath, a chamber, and a funnel for loading the needle with the pellets.

In certain embodiments, the funnel or the chamber can be transparent or translucent.

In a particular embodiment of this aspect, the funnel can include a tab for mounting the funnel to the chamber. The chamber can include a retainer for opening or closing the chamber thereby allowing the pellets to flow from the funnel to the needle in a sterile environment.

In another non-limiting aspect of the present invention, a scalpel includes a housing. The housing can have a tab and a channel therein. A blade can include an aperture for mounting the blade to the tab within the housing. A sheath can include an internal stop and a distal aperture. A spring can be mounted within the channel and against the stop between the sheath and the housing. When the scalpel is in a storage condition, the sheath covers the blade. When the sheath is pressed against a patient, or any hard surface, the housing can slide towards the sheath and establish a cutting position thereby allowing a portion of the blade to protrude through the distal aperture thereby forming a predetermined incision.

In some embodiments, the blade can retract into said sheath after use and lock in place thereby maintain sterility and ensuring proper disposal of the scalpel.

In certain embodiments, the predetermined incision can have a predetermined depth and predetermined width when said scalpel is in said cutting position In another aspect of the instant invention, a kit can include a pellet implantation device and a scalpel. The device can include a housing. The housing can have a first aperture and a second aperture. A slider tab can be recessed in the first aperture and slidably connected to the housing. A capture bracket can be connected to the slider tab. The capture bracket can include a first flange. A ram can be mounted within the housing. The ram can include a second flange for mounting a spring. A needle can include a distal flange and a proximal end. The distal flange can be mounted within the second aperture of the housing. The needle can be configured to store pellets therein.

The scalpel can include a housing. The housing can have a tab and a channel therein. A blade can include an aperture for mounting the blade to the tab within the housing. A sheath can include an internal stop and a distal aperture. A spring can be mounted within the channel and against the stop between the sheath and the housing. When the scalpel is in a storage condition, the sheath covers the blade and when sheath is pressed against a patient, the housing can slide towards the sheath and establish a cutting position thereby allowing a portion of the blade to protrude through the distal aperture thereby forming a predetermined incision.

In one embodiment of this aspect, the capture bracket can include a locking tab and the pellet implantation device housing can include a recess for capturing the locking tab to lock the device so that after one retraction of the needle, the device will not function.

In another embodiment, the needle can include a spring clip mounted within an aperture. The spring clip can retain the pellets within the needle prior to the pellets being dispensed.

In some embodiments, the kit can include a needle sheath.

In other embodiments, the kit can include a needle sheath, a chamber, and a funnel for loading the needle with pellets.

In certain embodiments, the funnel or the chamber can be transparent or translucent.

In yet other embodiments, a funnel can include a tab for mounting the funnel to a chamber, and the chamber can include a retainer for opening the chamber thereby allowing pellets to flow from the funnel to a needle. The funnel or the chamber can be transparent or translucent.

In some embodiments, the blade retracts into the sheath and locks in place after one use thereby maintain sterility and ensuring proper disposal of said scalpel.

In certain embodiments, the blade can protrude into the predetermined incision with a predetermined depth and a predetermined width when the scalpel is in the cutting position.

BRIEF DESCRIPTION OF THE DRAWINGS

FIG. 23 is a side view of some of the elements of the scalpel of FIG. 17 shown in the closed or sheathed position.

FIG. 24 is another side view of some of the elements of the scalpel of FIG. 17 shown in the closed or sheathed position.

DETAILED DESCRIPTION

Figure 1:
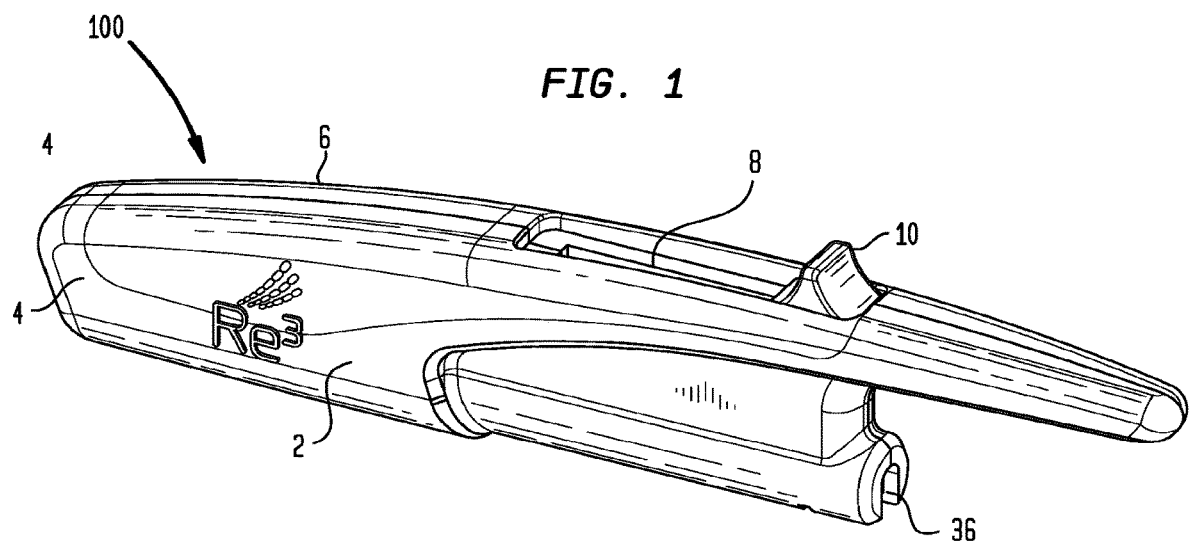
FIG. 1 is an isometric view of some of the elements of one embodiment of the implantation device included in the present invention.
Figure 2:
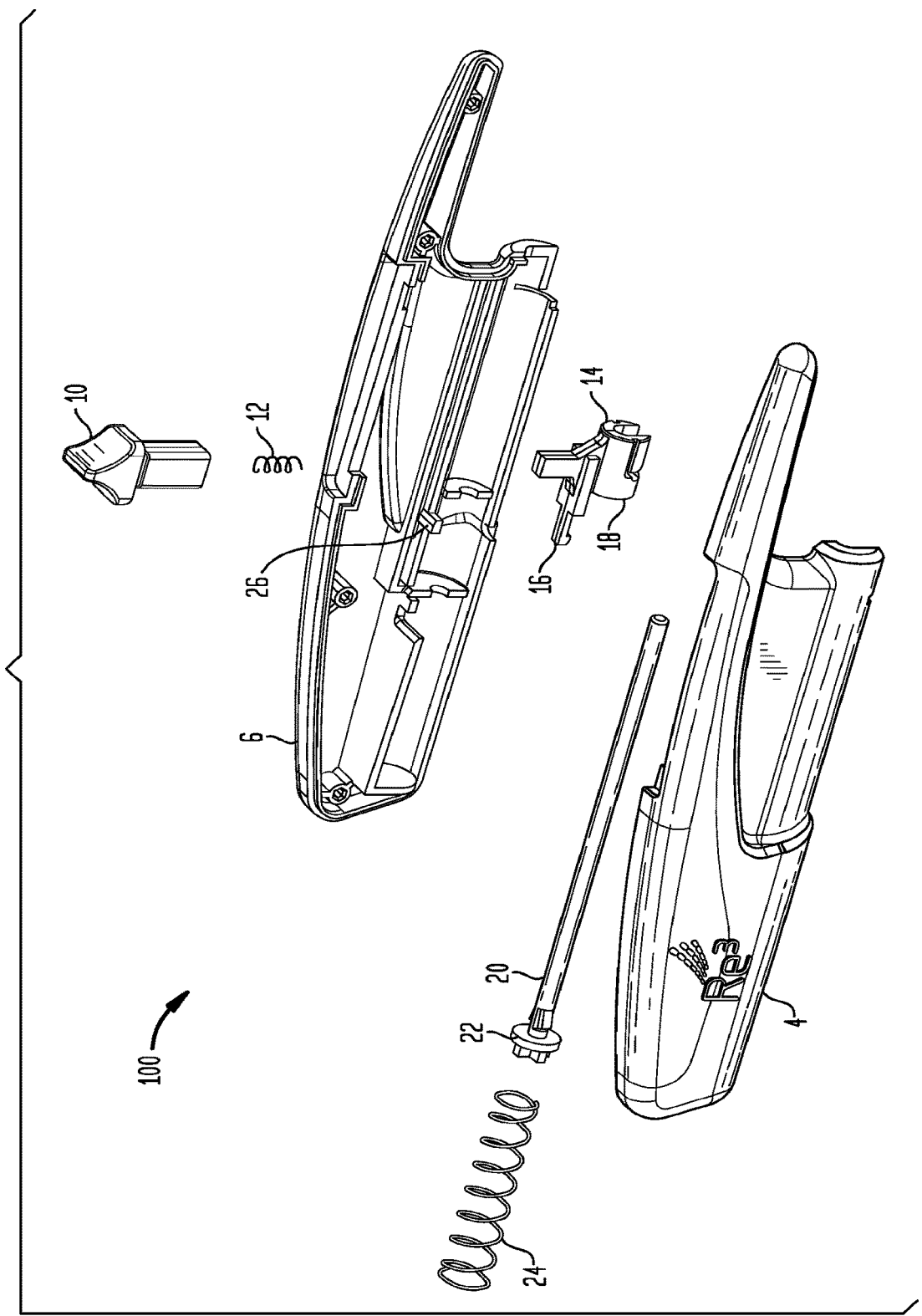
FIG. 2 is an exploded view of some of the elements of the device according to one embodiment of the present invention.

As used herein, the terms pellet refers to any size or shape of medicament used in treatment by a subcutaneous placement route. The terms pellet, medicine or medication may be singular or plural and are used interchangeably herein.

As used herein, the terms pellet refers to any prescription or over-the-counter medications, dietary supplements such as vitamins, minerals or cosmetic products. Further, the terms pill, medicine and or medication refer to any product in pelletized form which the user has a need or desire to use on a predetermined, scheduled basis for sustained release over a period of time when administered subcutaneously.

Some of the components of a non-limiting embodiment of the invention as described below may include the following elements: implantation device 100, housing 2, having a first half 4, and a second half 6, aperture 8, slider tab 10, spring 12, capture bracket 14, locking tab 16, flange 18, ram 20, flange 22, spring 24, recess 26, needle 28, flange 30, spring clip 32, aperture 34, needle end 29, pellets 200, skin 202, sheath 40, chamber 42, funnel 44, tabs 50, retainer 48, scalpel 300, housing 302, top half 304, bottom half 306, blade 308, aperture 310, tab 312, channel 314, lockout ramp 315, spring 316, sheath 318, top half 320, bottom half 322, aperture 324, stop 330, blade depth 332, blade width 334.

In one non-limiting embodiment of the present invention as shown in FIGS. 1-7, device 100 includes housing 2, having a first half 4 and a second half 6. The housing can snap together. Housing 2 includes an aperture 8 for slider tab 10. The slider tab 10 is connected via spring 12 to capture bracket 14. Bracket 14 includes a locking tab 16 and a flange 18. Bracket 14 can translate within the housing. Bracket 14 engages ram 20 via flange 22 such that flange 22 of ram 20 engages flange 18 of bracket 14. The ram is connected to spring 24 which biases the ram in either a deployed condition for deployment of pellets or in a stored condition for loading of a needle or disposal as explained below. When bracket 14 is retracted, tab 16 can engage recess 26 in the housing to lock the bracket in place thereby preventing more than one use of the device thus maintaining sterility.

Figure 3:
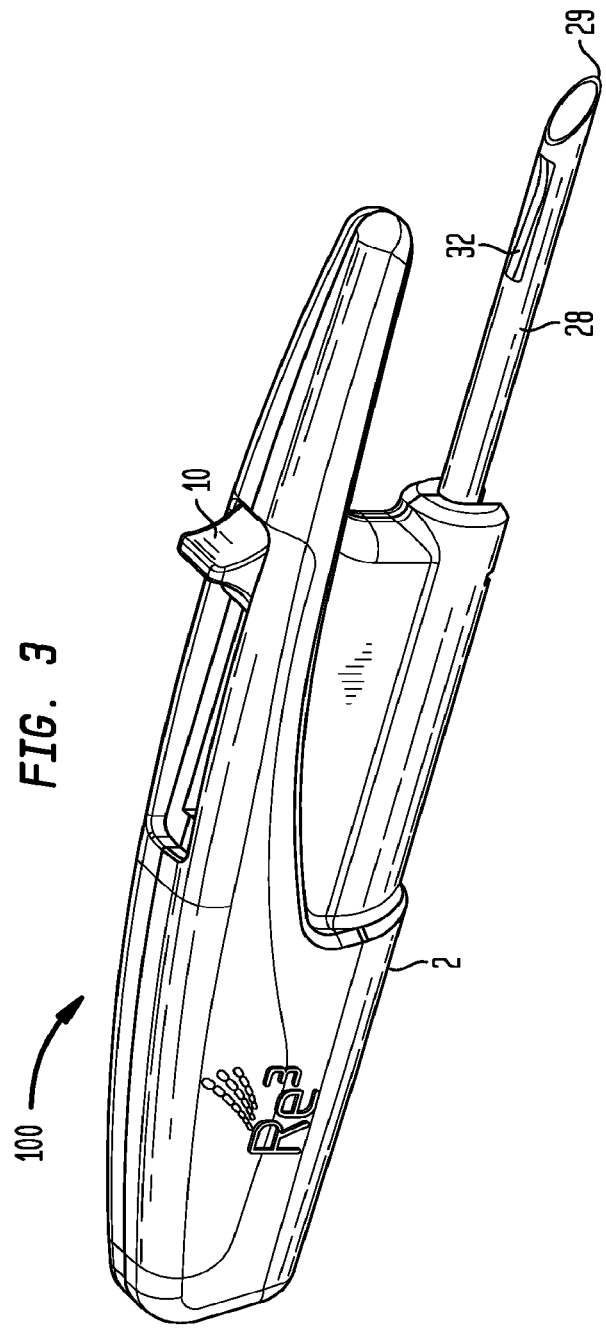
FIG. 3 is an isometric view depicting some of the elements of the implantation device including the needle.
Figure 4:
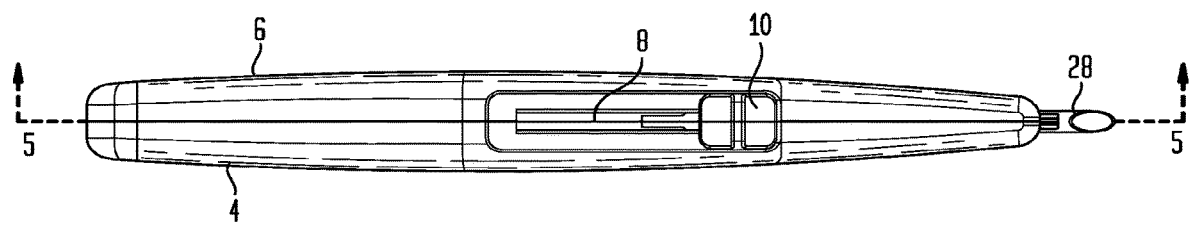
FIG. 4 is a top view depicting some of the elements included in the implantation device.
Figure 5:
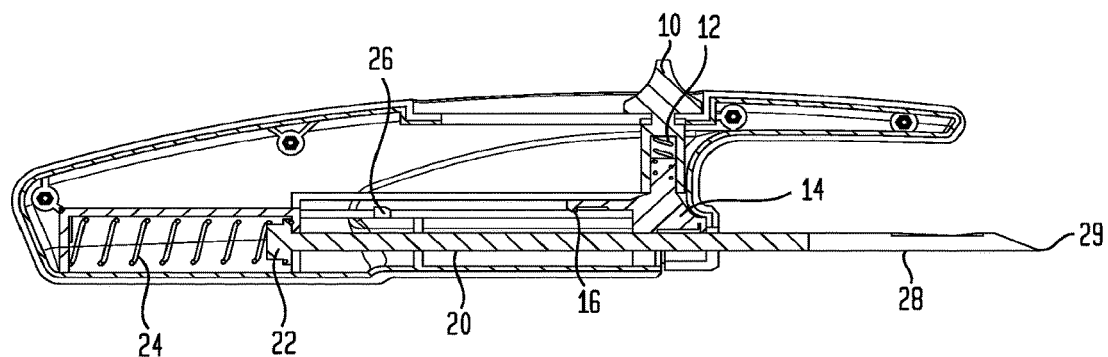
FIG. 5 is a cross-sectional view depicting of some of the elements included in the device shown in FIG. 4.
Figure 6:
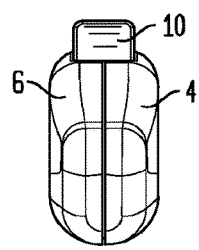
FIG. 6 is a rear view depicting of some of the elements included in the device of FIG. 4.
Figure 7:
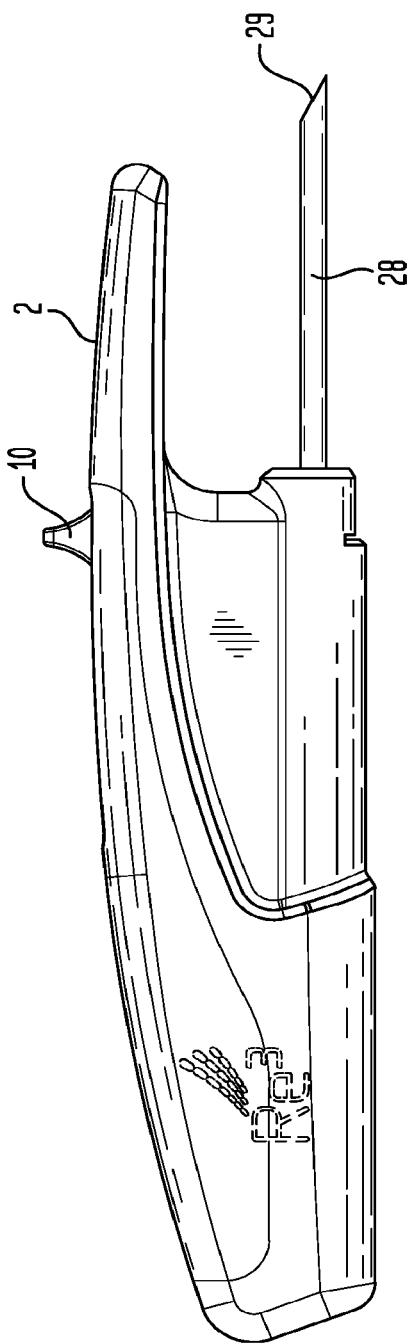
FIG. 7 is a side view of some of the elements included in the interactive medication management device of FIG. 4.
Figure 8:
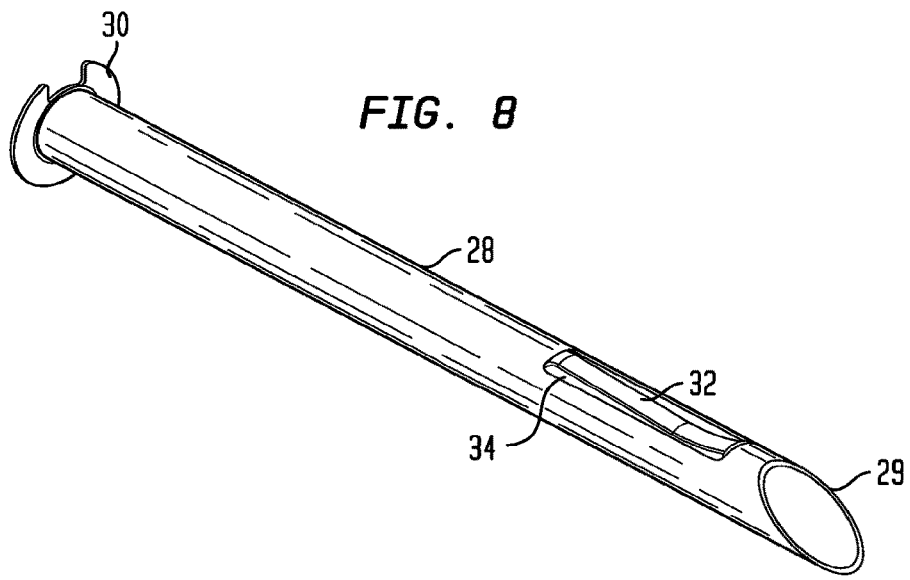
FIG. 8 an isometric view of the needle included in the implantation device of the instant invention.
Figure 9:
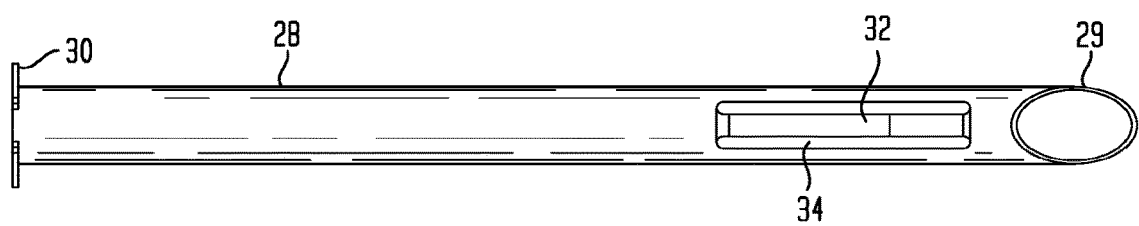
FIG. 9 is a top view of the needle shown in FIG. 8.
Figure 10:
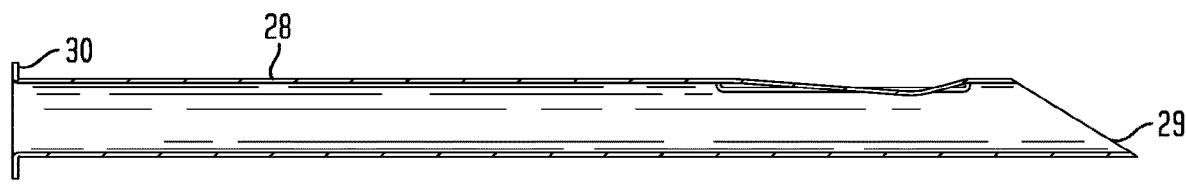
FIG. 10 is a side view of the needle shown in FIG. 8.
Figure 11:
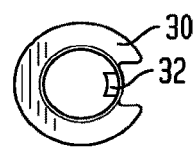
FIG. 11 is a rear view of the needle shown in FIG. 8.
Figure 12:
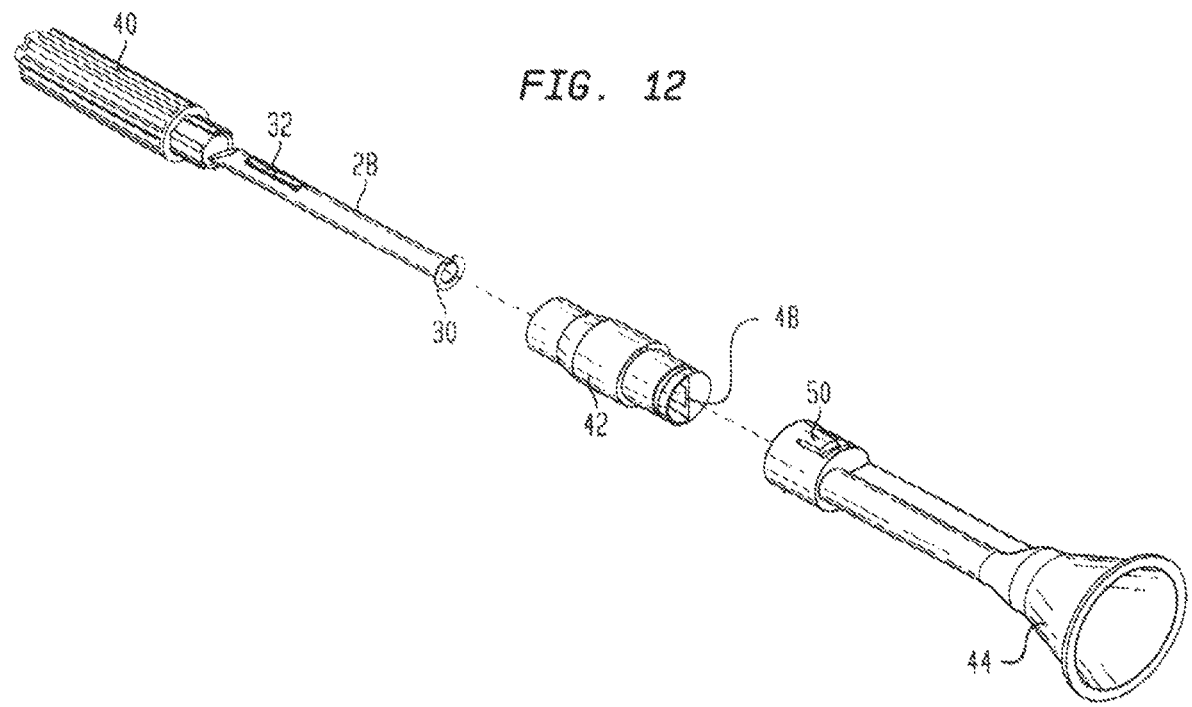
FIG. 12 is an isometric exploded view of some of the elements used for filling and protecting the needle of the instant device.
Figure 13:
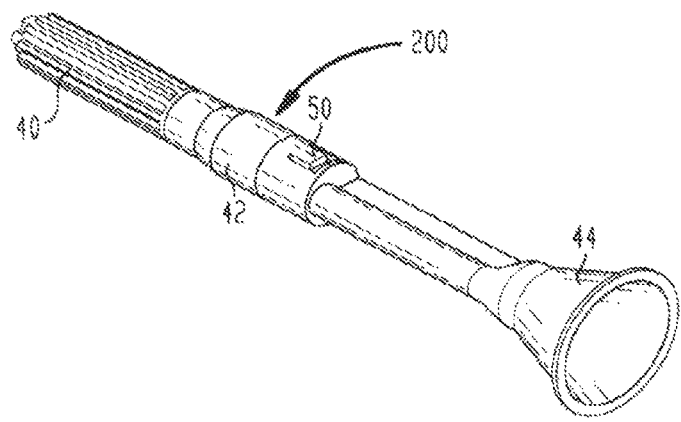
FIG. 13 is an isometric view of some of the elements used for filling and protecting the needle of the instant device in an assembled or needle filling configuration.
Figure 14:
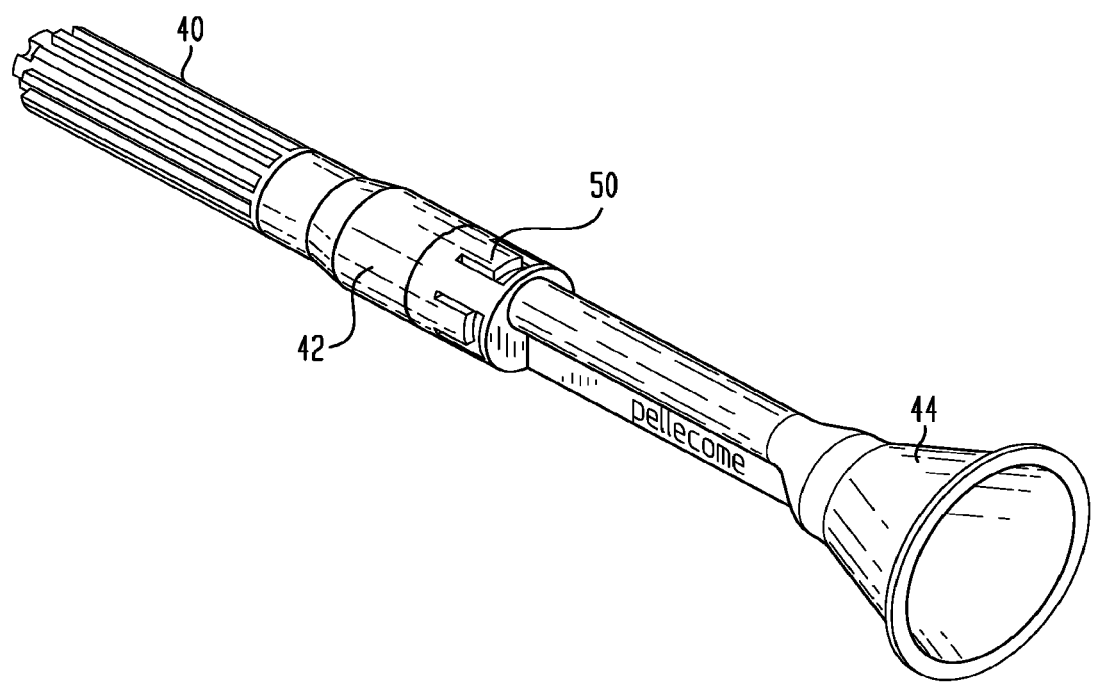
FIG. 14 is another isometric view of some of the elements used for filling and protecting the needle of the instant device in an assembled or needle filling configuration.
Figure 15:
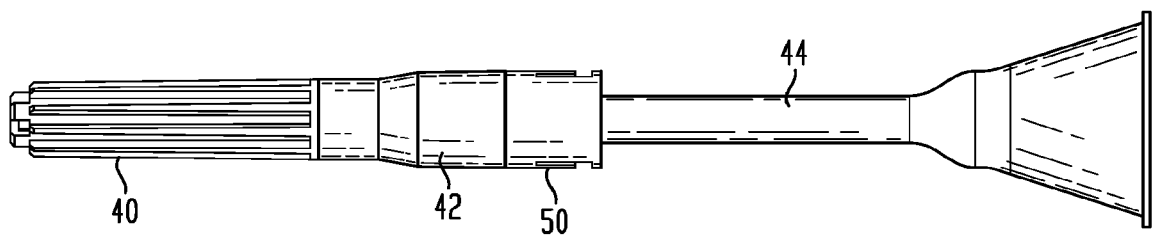
FIG. 15 is a top view of some of the elements used for filling and protecting the needle of the instant device in an assembled or needle filling configuration.
Figure 16:
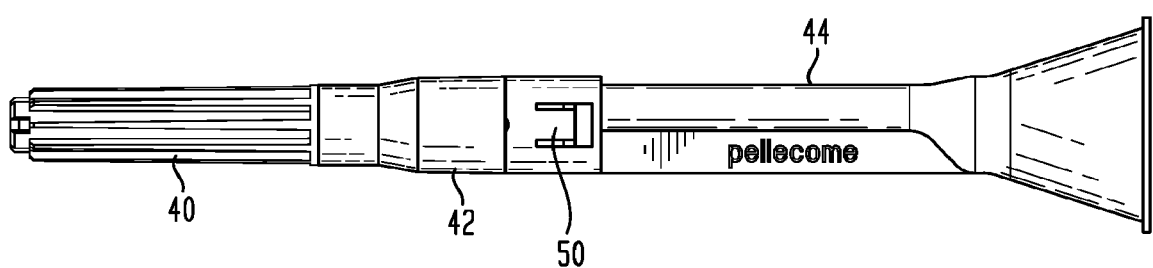
FIG. 16 is a side view of some of the elements used for filling and protecting the needle of the instant device in an assembled or needle filling configuration.
Figure 26:
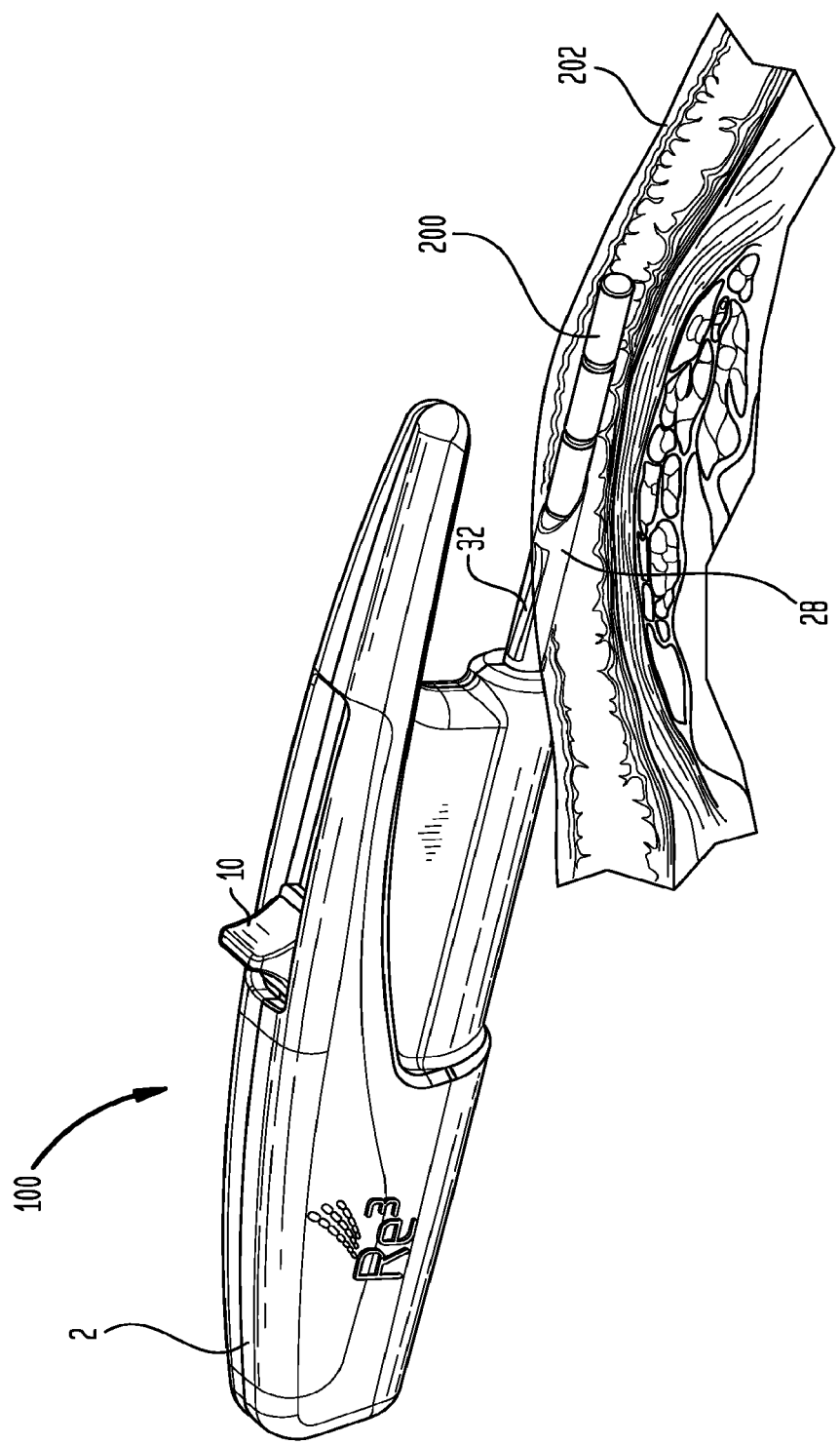
FIG. 26 is an isometric view of some of the elements of an implantation device depicting subcutaneous pellet implantation.

As shown in FIG. 3, and more particularly in FIGS. 8-11, the device includes a hollow needle 28 that fits within aperture 36 of the housing. Needle 28 includes flange 30 and spring clip 32 which is located within aperture 34 in the body of needle 28. Needle 28 can have a diagonally cut shaped end 29 to facilitate delivery of pellets 200 under the skin 202 as discussed below. See FIG. 26

Referring to FIGS. 12-16, needle 28 can be enclosed to fill the needle with pellets 200 for subcutaneous placement and for maintaining sterility and protecting the user from the sharp needle which is critical.

Sheath 40, a transfer chamber 42, and a loading and verification funnel 44. The sharp end of the needle is enclosed in sheath 40. The chamber 42 mates to flange of the needle. Funnel 44 is preferably made of a transparent or translucent material to allow a user to view pellets within the funnel in order to verify the condition, type, color, number, etc. of pellets to be loaded in the needle prior to insertion. The user can open a sterile package of pellets and pour or place them into the loading funnel 44. The loading funnel mates with the chamber 42 such that the pellets are prevented from entering the chamber until the user decides to load. Tabs 50 align the funnel and the chamber so that the funnel will retain pellets until inspection can be performed. When the user is ready, the funnel can be rotated about 180 degrees in relation to the chamber, thereby allowing retainer 48 to move into a position that allows the pellets to drop through the chamber into the body of the needle. It will be appreciated that the rotation angle can be adjusted to include any angle that creates a space large enough to allow a medicament, pellets for example, to fall from the funnel and the chamber. A preferred range is about 90 to about 180 degrees. The pellets will fall into the needle via gravity and self-align in a row in position for insertion. Spring clip 32 maintains the pellets within the needle and does not allow them to exit the needle until the user activates the ram as discussed below.

In operation, a user obtains a sterile package of pellets. The user can empty the package into the sterile loading funnel which retains the pellets and allows for visual inspection. After inspection, the user rotates the funnel in relation to the chamber which allows the pellets to fall into the needle 28 and be retaining in a single row as discussed above.

When the user is ready, after a proper size incision is made as will be discussed below, the funnel 44 and loading chamber 42 can be removed from the needle 28. The needle can be loaded into the housing to engage flange 30 with aperture 36 in the housing. The sterile sheath 40 can be removed prior to insertion thereby protecting the needle from contamination and protecting the user from injury. When the needle is inserted into the housing the spring 24 loaded ram 20 slides forward and locks into place. The ram gently urges the pellets to the front of the needle as the needle is retracted and locks the needle into the housing so it cannot be removed.

The operator can now insert the needle into a patient at the proper depth and location. Once positioned, the user engages slider tab 10 which translates in the housing. Slider 10 engages the capture bracket 14 to retract the needle via flange 30. While the needle is being retracted, ram 20 translates through the center of the needle and urges against the pellets thereby causing the pellets to be smoothly and gently deposited at the chosen deposition cite in a single row, thus avoiding any damage to the pellets.

The spring clip 32 prevents the pellets from falling out inadvertently. During deposition, the spring clip is designed to deflect and allow the pellets to pass through the needle while avoiding damage of the pellets.

In operation, loading the device 100 with pellets 200 was also designed to be easy, maintaining sterility of the pellets at all times. The pellets can be separately pre-packed in a sterile vial.

After the user removes the cap from the pellet vial, the vial is aligned with the funnel on the needle sheath, so that the pellets can be downloading into the needle as discussed above.

After needle is inserted and locked into the housing the sheath can be removed. A precise incision, having a specific width and depth must be made on a preselected area for pellet insertion.

Referring to FIGS. 17-25, a sterile, safety scalpel 300 for use with inserting tool 100 is described. Scalpel housing 302, can include a top half 304 and a bottom half 306. The halves 302 and 304 can be assembled together to form the scalpel housing and retain the blade 308. Blade 308 includes an aperture 310 that fits on tab 312 in the bottom housing 306. Thus, the blade is captured in a fixed stable position within the housing.

Figure 18:
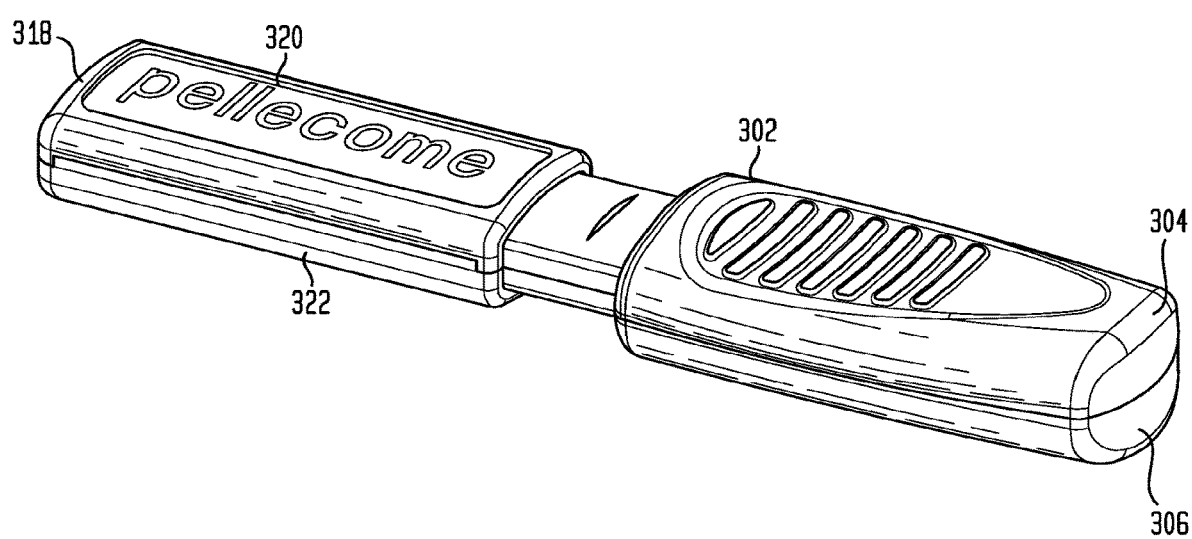
FIG. 18 is an isometric view of some of the elements of the scalpel of FIG. 17 shown in the closed or sheathed position.
Figure 19:
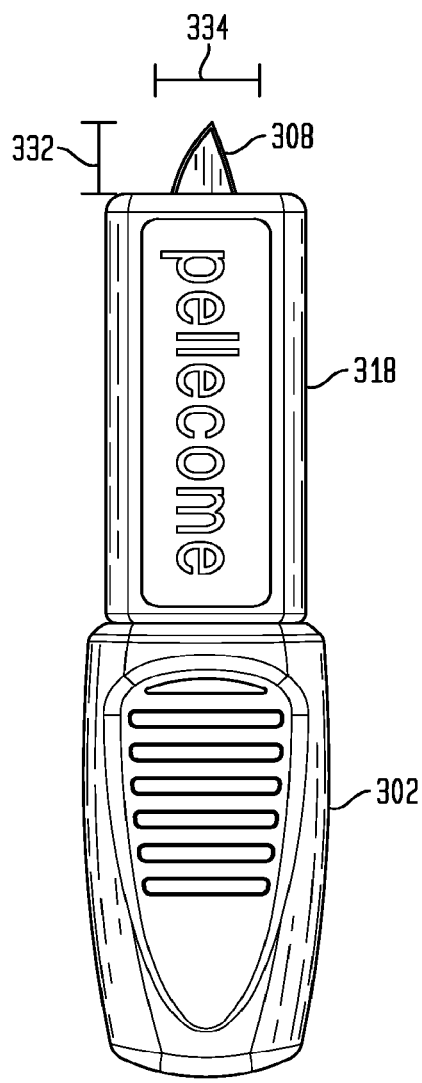
FIG. 19 is a side view of some of the elements of the scalpel of FIG. 17 shown in the open or unsheathed position.
Figure 20:
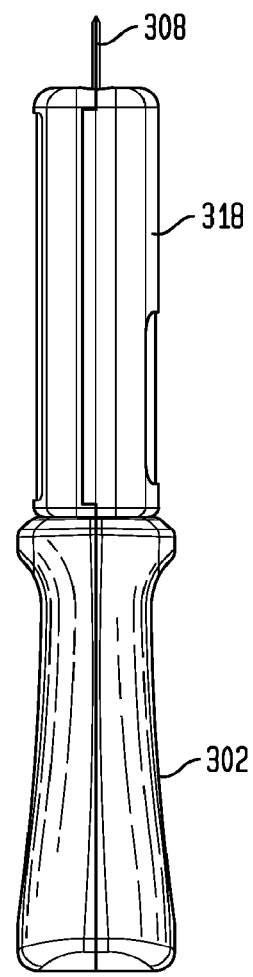
FIG. 20 is another side view of some of the elements of the scalpel of FIG. 17 shown in the open or unsheathed position.
Figure 21:
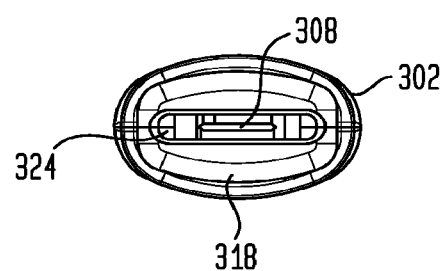
FIG. 21 is a top view of some of the elements of the scalpel of FIG. 17 shown in the open or unsheathed position.
Figure 22:
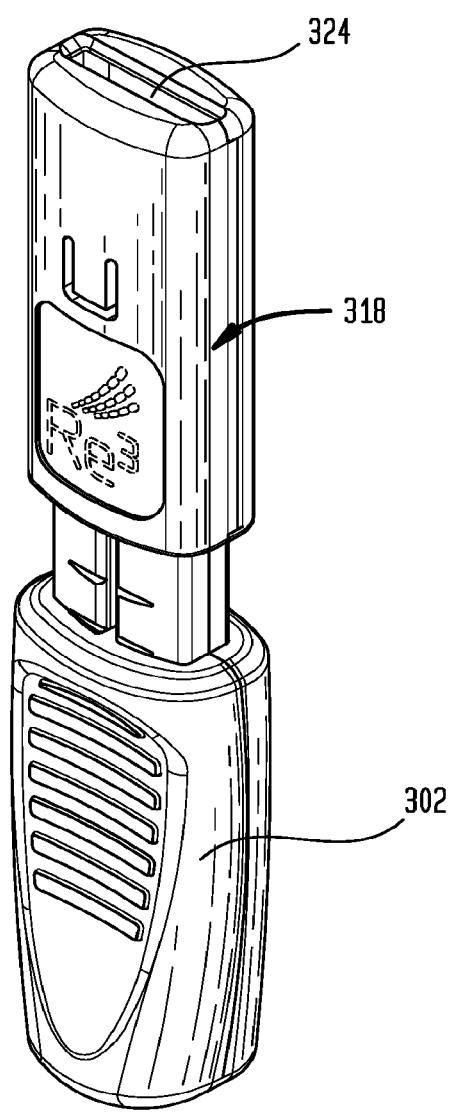
FIG. 22 is an isometric view of some of the elements of the scalpel of FIG. 17 shown in the closed or sheathed position.
Figure 25:
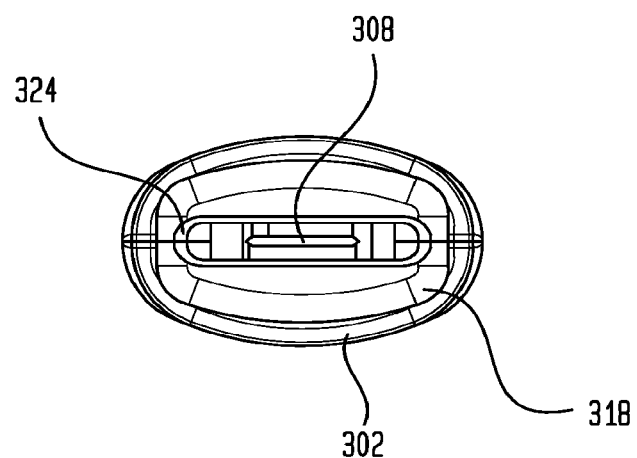
FIG. 25 is a top view of some of the elements of the scalpel of FIG. 17 shown in the closed or sheathed position.

Spring 316 fits within the top side of channel 314 (the reverse side including the protruding tab to lock the blade). Sheath 318 includes top and bottom halves 320 and 322 which lock together to form a solid sheath for blade 308. When assembled, the sheath includes an aperture 324 (See FIG. 22) to allow a predetermined portion of blade 308 to protrude. By predetermining a portion of the blade that protrudes, the operator can control the precise depth and with of the incision. Spring 316 holds the sheath 318 in a safe sterile position such that the blade is covered as shown in FIG. 18.

In the resting position, scalpel 300 is closed, that is, the blade does not protrude and the sheath protects the blade and the user while maintain sterility. The operator holds the scalpel with the sheath resting against the preselected incision site on the skin and moves the housing in the direction of the sheath. This motion causes spring 316 to compress which allows the blade and housing to move through the sheath a preselected distance. When the housing contacts stop 330 in the sheath, the blade and housing will stop moving thereby allowing a portion of the blade to protrude from the sheath. Since the device is held against the skin, the protruding portion of the blade will cut through the skin to a precise depth 332 and width 334 thereby forming a predetermined incision size.

Figure 17:
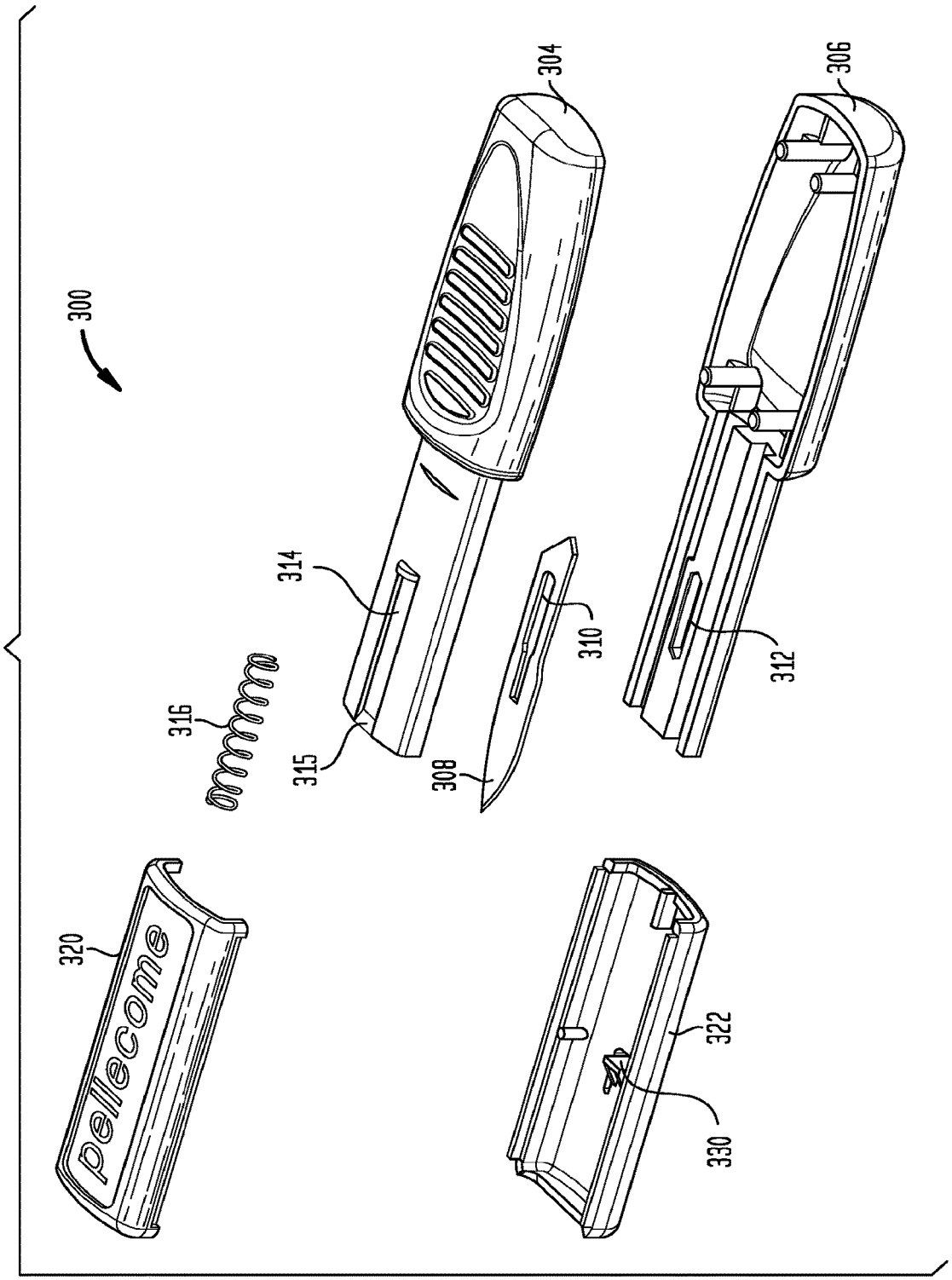
FIG. 17 is an exploded view of a scalpel used in the tool kit of the instant invention.

After use, the spring returns to an uncompressed position and the user pulls on the sheath to extend it further than it would otherwise travel on its own. In doing so this forces the stop 330 to deflect and ride over the lockout ramp 315 as shown in FIG. 17. Once the stop has moved past the ramp, the stop 330 cannot travel back over the ramp 315, effectively locking out the sheath in the extended closed position.

By using the lockout feature, the scalpel can be a single use product. After the surgeon in finished making the incision, the sheath is locked in a closed position and cannot be reopened because the sheath cannot travel beyond the lockout ramp. Thus, a sterile product is ensured. Further, the lockout feature prevents inadvertent injury due to exposure to an open blade and thus protects the user.

Next the needle can be inserted through the incision and into the patient, and the pellets deposited as discussed above. After the needle is removed, the incision can be closed with, for example, surgical glue, sutures, or the like.

Although the invention herein has been described with reference to particular embodiments, it is to be understood that these embodiments are merely illustrative embodiments and that other arrangements may be devised without departing from the spirit and scope of the present invention as defined by the disclosure herein.

What is claimed is:

1. A pellet implantation device comprising:
   (a) a housing, said housing having a first aperture and a second aperture, said first and second apertures being substantially perpendicular to one another wherein said first aperture is parallel to a longitudinal axis of said housing;
   (b) a slider tab, said slider tab being recessed in said first aperture and slidably connected to said housing, said slider tab being configured to translate within said first aperture and to move substantially parallel to the longitudinal axis of said housing;
   (c) a capture bracket, said capture bracket being connected to said slider tab, said capture bracket including a recess;
   (d) a fixed ram, said fixed ram being mounted within said housing; and
   (e) a detachable retractable needle having a long axis substantially parallel to said housing, said needle including a distal end and a proximal end, said distal end being removably mountable within said capture bracket recess and removably connected to said capture bracket recess, said distal end being adapted to mount to a needle sheath and a funnel for filling said needle with at least one pellet prior to mounting said needle within said capture bracket recess, said needle being capable of being loaded with said at least one pellet from the distal end,
   wherein said retractable needle can be moved when said slider tab is depressed thereby allowing said slider tab, said capture bracket, and said needle to translate in relation to said housing and said fixed ram thereby dispensing said at least one pellet, wherein the longitudinal axis of said housing, and translation of said slider tab are substantially parallel to the long axis of the needle.

2. The pellet implantation device of claim 1, wherein said capture bracket includes a locking tab and said housing includes a recess for capturing said locking tab thereby locking said device wherein said needle can only be retracted once after a delivery of said at least one pellet to a patient.

3. The pellet implantation device of claim 1, wherein said needle includes a spring clip mounted within an aperture, said spring clip for retaining said at least one pellet within said needle prior to said at least one pellet being dispensed.

4. The pellet implantation device of claim 1, further including a needle sheath, said needle sheath configured to cover said proximal end of said retractable needle during loading of said at least one pellet prior to said retractable needle being mounted to said recess in said capture bracket.

5. The pellet implantation device of claim 1, further including a needle sheath, and a funnel configured for loading said retractable needle with said at least one pellet.

6. The pellet implantation device of claim 5, wherein said funnel includes a tab for mounting said funnel to said chamber, and said chamber includes a retainer for opening said chamber thereby allowing said at least one pellet to flow from said funnel to said retractable needle.

7. A scalpel comprising:
   (a) a housing, said housing having an external channel including a lockout ramp and an internal mounting tab;
   (b) a blade, said blade including an aperture for mounting said blade to said internal mounting tab within said housing;
   (c) a sheath, said sheath including an internal stop, and a distal aperture;
   (d) a spring, said spring being mounted within said channel and against said stop between said sheath and said housing, said spring causing said sheath to be biased in a resting position covering said blade when said spring is uncompressed and said spring being in a compressed position when said blade is exposed and resides in a position protruding beyond said sheath, wherein when said sheath is held against a patient said housing can be depressed by a user thereby causing said blade to form a plunge cut having a predetermined depth and width in said patient, and when said housing is released by the user, said spring causes said blade to retract to said resting position; and
   (e) wherein a user can manually translate said sheath longitudinally in a direction away from said housing to position said internal stop beyond said lockout ramp thereby encapsulating said blade within said sheath and irreversibly locking said sheath in a closed position to facilitate one time use and safe disposal of said scalpel.

8. The scalpel of claim 7, wherein said scalpel can form a predetermined incision having a predetermined depth and a predetermined width.

9. A kit comprising:
   (a) a pellet implantation device including a housing, said housing having a first aperture and a second aperture, said first and second apertures being substantially perpendicular to one another wherein said first aperture is parallel to a longitudinal axis of the housing, a slider tab, said slider tab being recessed in said first aperture and slidably connected to said housing, said slider tab being configured to translate within said first aperture and move substantially parallel to the longitudinal axis of the housing, a capture bracket, said capture bracket being connected to said slider tab, said capture bracket including a recess, a fixed ram, said ram being mounted within said housing, a needle, said needle including a distal a detachable retractable needle having a long axis, said needle including a distal end and a proximal end, said distal end being removably mountable within said capture bracket recess and removably connected to said capture bracket recess, said distal end being adapted to mount to a needle sheath and a funnel for filling said needle with at least one pellet prior to mounting said needle within said capture bracket recess, said needle being capable of being loaded with said at least one pellet from the distal end, wherein said retractable needle can be moved when said slider tab is depressed thereby allowing said slider tab, said capture bracket, and said needle to translate in relation to said housing and said fixed ram thereby dispensing said at least one pellet, wherein the longitudinal axis of the housing and translation of said slider tab are substantially parallel to the long axis of the needle; and (b) a scalpel including a housing, said housing having an external channel including a lockout ramp and an internal mounting tab, a blade, said blade including an aperture for mounting said blade to said internal mounting tab within said housing, a sheath, said sheath including an internal stop, an internal stop and a distal aperture, a spring, said spring being mounted within said channel and against said stop between said sheath and said housing, said spring causing said sheath to be biased in a resting position covering the when said spring is uncompressed and said spring being in a compressed position when said blade is exposed and resides in a position protruding beyond said sheath, wherein when said sheath is held against a patient said housing can be depressed by a user thereby causing said blade to form a cut having a predetermined depth and width in said patient, and when said housing is released by the user, said spring causes said blade to retract within said sheath, (c) wherein a user can manually translate said sheath longitudinally in a direction away from said housing to position said internal stop beyond said lockout ramp thereby encapsulating said blade within said sheath and irreversibly locking said sheath in a closed position to facilitate one time use and safe disposal of said scalpel.

10. The kit of claim 9, wherein said capture bracket includes a locking tab and said pellet implantation device housing includes a recess for capturing said locking tab.

11. The kit of claim 9, wherein said needle includes a spring clip mounted within an aperture, said spring clip for retaining said pellets within said needle prior to said at least one pellet being dispensed.

12. The kit of claim 9, further including a needle sheath, said sheath configured to cover said proximal end of said needle thereby allowing access to said distal end of said needle for filling said needle with said at least one pellet before mounting said needle in said recess.

13. The kit of claim 9, further including a needle sheath, and a funnel for loading said needle with said at least one pellet.

14. The kit of claim 13, wherein said funnel includes a tab for mounting said funnel to a chamber, and said chamber includes a retainer for opening said chamber thereby allowing said pellets to flow from said funnel to said needle.

15. The kit of claim 9, wherein said blade protrudes into a predetermined incision with a predetermined depth and a predetermined width when said scalpel is in a cutting position.

* * * * *